(12) United States Patent
Afzali-Ardakani et al.

(10) Patent No.: US 8,999,739 B2
(45) Date of Patent: *Apr. 7, 2015

(54) FIELD EFFECT TRANSISTOR-BASED BIO-SENSOR

(71) Applicant: International Business Machines Corporation, Armonk, NY (US)

(72) Inventors: Ali Afzali-Ardakani, Ossining, NY (US); Christopher P. D'Emic, Ossining, NY (US); Ashish Jagtiani, Tarrytown, NY (US); Sufi Zafar, Briarcliff Manor, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/965,346

(22) Filed: Aug. 13, 2013

(65) Prior Publication Data

US 2014/0179047 A1    Jun. 26, 2014

Related U.S. Application Data

(63) Continuation of application No. 13/723,514, filed on Dec. 21, 2012.

(51) Int. Cl.
*H01L 21/00*    (2006.01)
*G01N 27/414*    (2006.01)
(Continued)

(52) U.S. Cl.
CPC ...... *G01N 27/4145* (2013.01); *H01L 29/66477* (2013.01); *H01L 29/786* (2013.01)

(58) Field of Classification Search
CPC .................. G01N 27/4145; H01L 29/66477
USPC ..................... 438/289, 49; 257/253
See application file for complete search history.

(56) References Cited

U.S. PATENT DOCUMENTS

| | | | |
|---|---|---|---|
| 7,064,372 B2 | 6/2006 | Duan et al. | |
| 7,067,867 B2 | 6/2006 | Duan et al. | |

(Continued)

FOREIGN PATENT DOCUMENTS

| | | |
|---|---|---|
| EP | 2426487 A1 | 3/2012 |
| WO | 2012078340 A1 | 6/2012 |

OTHER PUBLICATIONS

Stern, Eric et al., "Label-free immunodetection with CMOS-compatible semiconducting nanowires", Nature, Feb. 1, 2007, vol. 445, pp. 519-522.

(Continued)

*Primary Examiner* — Olik Chaudhuri
*Assistant Examiner* — Christine Enad
(74) *Attorney, Agent, or Firm* — Harrington & Smith; Louis J. Percello (57) ABSTRACT

An apparatus comprises: a sensing element formed on a buried oxide layer of a substrate and providing communication between a source region and a drain region; a gate dielectric layer on the sensing element, the gate dielectric layer defining a sensing surface on the sensing element; a passive surface surrounding the sensing surface; and a compound bound to the sensing surface and not bound to the passive surface, the compound having a ligand specifically configured to preferentially bind a target molecule to be sensed. An electrolyte solution in contact with the sensing surface and the passive surface forms a top gate of the apparatus.

6 Claims, 5 Drawing Sheets

(51) Int. Cl.
*H01L 29/66* (2006.01)
*H01L 29/786* (2006.01)

(56) References Cited

U.S. PATENT DOCUMENTS

| | | | |
|---|---|---|---|
| 7,135,728 | B2 | 11/2006 | Duan et al. |
| 7,233,041 | B2 | 6/2007 | Duan et al. |
| 7,262,501 | B2 | 8/2007 | Duan et al. |
| 7,427,328 | B2 | 9/2008 | Duan et al. |
| 7,692,219 | B1 * | 4/2010 | Holm-Kennedy ............ 257/253 |
| 7,851,841 | B2 | 12/2010 | Duan et al. |
| 7,932,511 | B2 | 4/2011 | Duan et al. |
| 8,013,366 | B2 | 9/2011 | Lee et al. |
| 8,030,186 | B2 | 10/2011 | Romano et al. |
| 2008/0230849 | A1 * | 9/2008 | Afzali-Ardakani et al. .. 257/391 |
| 2009/0085072 | A1 * | 4/2009 | Lee et al. ..................... 257/253 |
| 2009/0263072 | A1 * | 10/2009 | Albert et al. .................... 385/13 |
| 2011/0033952 | A1 | 2/2011 | Khater et al. |
| 2011/0163812 | A1 * | 7/2011 | Bansal et al. ................. 330/277 |

OTHER PUBLICATIONS

Knopfmacher, O., et al., "Nernst Limit in dual-Gated Si-Nanowire FET Sensors", Nano Letters, 2010, pp. 2268-2274.
Gao, Xuan P.A., et al., "Subthreshold Regime has the Optimal Sensitivity for Nanowire FET Biosensors", Nano Letters, 2009, 6 pgs.
Zheng, Gengfeng, et al., "Multiplexed electrical detection of cancer markers with nanowire sensor arrays", Nature Biotechnology, vol. 23, No. 10, Oct. 2005, pp. 1294-1301.
Cui, Yi, et al., Nanowire Nanosensors for Highly Sensitive and Selective Detection of Biological and Chemical Species, Science, vol. 293, No. 5533, Aug. 17, 2001, pp. 1289-1292.

* cited by examiner

FIELD EFFECT TRANSISTOR-BASED BIO-SENSOR

CROSS REFERENCE

This application is a continuation of and claims priority to U.S. patent application Ser. No. 13/723,514, filed on Dec. 21, 2012, the contents of which are incorporated herein by reference in their entirety.

BACKGROUND

The exemplary embodiments of this invention relate generally to bio-sensors and, more particularly, to bio-sensors based on field effect transistors.

Sensors based on field effect transistors (FETs) can be used in a variety of different bio-sensing applications to detect various biomolecules. In such sensors, a sensing surface is modified with a functional group that acts as a receptor to bind a target species having a charge. The target species may be any biomolecule such as a protein, virus, drug moeity, or the like. The charge of the bound target species on the sensing surface causes change in the drain current that can be used in a bio-sensing application.

The sensitivity of a FET-based bio-sensor is generally limited due to the probability of an unbound target species attaching to the sensing surface. In the case of typical sensors, both sensing and non-sensing (also known as passive) surfaces are of the same material (i.e. $SiO_2$) and therefore have the same chemistry. Hence, an unbound target species in a solution can bind to both sensing and passive surfaces. The sensitivity depends on the ratio $A_{sense}/A_{passive}$ where $A_{sense}$ is the sensing surface area and $A_{passive}$ is the passive surface area. Since the passive surface area is significantly larger than the sensing surface area (e.g., generally on the order of $10^3$ to $10^4$ times as large) and since the surfaces are of the same chemistry, the majority of target species would attach to the passive surface and not to the sensing surface. Based on the construction of bio-sensors of this type, a particular molecule of a target species in dilute concentrations may not be detected due to the low probability of such a molecule binding to the sensing surface, thereby providing inaccurate detection readings. Consequently, having sensing and passive surfaces of disparate surface areas and of the same material limits the sensitivity of a FET-based bio-sensor.

BRIEF SUMMARY

In one exemplary aspect, an apparatus comprises: a sensing element formed on a buried oxide layer of a substrate and providing communication between a source region and a drain region; a gate dielectric layer on the sensing element, the gate dielectric layer defining a sensing surface on the sensing element; a passive surface surrounding the sensing surface; and a compound bound to the sensing surface and not bound to the passive surface, the compound having a ligand specifically configured to preferentially bind a target molecule to be sensed. An electrolyte solution in contact with the sensing surface and the passive surface forms a top gate of the apparatus.

In another exemplary aspect, an SOI finFET-based sensor comprises: a sensing element formed on a substrate having a source region and a drain region, the sensing element comprising a silicon member extending between the source region and the drain region; a gate dielectric layer formed over the sensing element, the gate dielectric layer comprising a sensing surface over the sensing element; a passive surface surrounding, adjacent to, or around the sensing surface, a material of the passive surface being dissimilar to a material of the sensing surface; and a hydroxamic acid bound to the sensing surface, the hydroxamic acid having a ligand specifically configured to bind a target molecule to be sensed. The SOI finFET-based sensors are exemplary, as the embodiments described herein are applicable to all other types of FET sensors such as bulk FETs, planar FETs, and the like.

In another exemplary aspect, a method of forming a sensor comprises: disposing a silicon sensing element on a substrate; depositing a gate dielectric layer on the silicon sensing element, the gate dielectric layer forming a sensing surface on the silicon sensing element; depositing a passive surface on the substrate surrounding, adjacent to, or around the sensing surface, a material of the passive surface being different from a material of the sensing surface; and modifying the sensing surface with a compound to receive a target species.

BRIEF DESCRIPTION OF THE SEVERAL VIEWS OF THE DRAWINGS

The foregoing and other aspects of exemplary embodiments are made more evident in the following Detailed Description, when read in conjunction with the attached Drawing Figures, wherein.

DETAILED DESCRIPTION

Exemplary embodiments of a FET-based sensor fabricated on a silicon-on-insulator (SOI) substrate and methods related to the fabrication thereof are disclosed herein. The SOI FET-based sensor comprises lightly-doped fin-shaped silicon forming a channel, heavily doped source and drain regions, and a gate dielectric layer covering the three sides of the silicon fin. The gate dielectric surface is a sensing surface, and detection occurs when target molecules bind to the gate dielectric surface. All surfaces other than the gate dielectric are referred as passive surfaces because no detection occurs when target molecules bind to them. The gate dielectric layer comprises a first material (e.g., $HfO_2$) that is different from that of the passive surfaces, which comprises a second material (e.g., $SiO_2$). An electrolyte solution in contact with the sensing and passive surfaces forms a top gate of the apparatus.

Since the FET-based sensor is fabricated on SOI substrate, it has a buried oxide layer on the substrate. The substrate forms the back gate.

Since the sensing and passive surfaces are of different materials with different surface chemistries, this difference provides a means to selectively modify the sensing surface by using a self-assembly method such that the target molecules preferentially bind to the sensing surface. To achieve this selective modification, molecules with two key attributes are used for self-assembly: (i) a molecule preferentially binds to the gate dielectric surface in comparison to the passive surface, and (ii) the molecule has a ligand that preferentially binds the target molecule.

As an example, selective modification the $HfO_2$ sensing surface with $SiO_2$ as the passive surface such that the target protein streptavidin would only bind to the sensing surface is demonstrated as follows: (1) hydroxamic acid compound with biotin as the ligand is used in the self-assembly process; (2) hydroxamic acid preferentially binds to the $HfO_2$ sensing surfaces in comparison to the $SiO_2$ passive surfaces, and biotin preferentially binds to the target protein streptavidin; (3) a solution of biotin hydroxamic acid compound is formed, and the sensing and surrounding passive surfaces are exposed to the solution for several hours; and (4) during the exposure time, biotin hydroxamic acid molecules attach themselves preferentially to the $HfO_2$ sensing surface. It may be noted that to detect another type of target protein, the biotin may be replaced with another molecule which would specifically bind the new target protein.

The SOI fin FET-based sensors are exemplary, as the embodiments described herein are applicable to all other types of FET sensors such as bulk FETs, planar FETs, and the like. In any embodiment, the gate dielectric sensing and passive surfaces are of two different materials, and the surface materials are chosen such that selective surface modification can occur easily via the self-assembly method.

Figure 1:
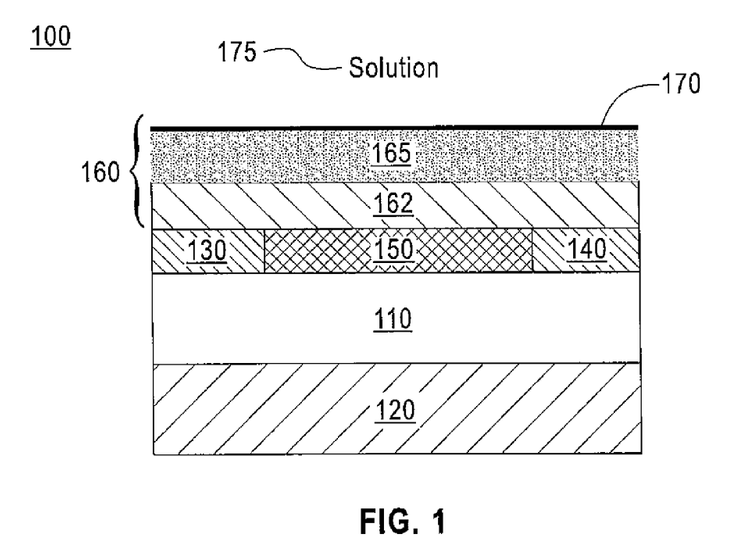
FIG. 1 is a side view of a FET-based sensor.

As shown in FIG. 1, one exemplary embodiment of a FET-based sensor for use as a bio-sensor is designated generally by the reference number 100 and is hereinafter referred to as "sensor 100." Sensor 100 comprises a substrate 120, a buried oxide layer 110 formed on the substrate 120, a sensing element 150 disposed on the buried oxide layer 110 between a source region 130 and a drain region 140, and a gate dielectric layer 160 deposited on the sensing element 150 and the source region 130 and drain region 140. The gate dielectric layer 160 comprises a dielectric layer 162 and a layer of metal oxide 165, which may be arranged as two distinct layers or as a single layer. An exposed surface of the metal oxide 165 defines a sensing surface 170. A solution 175 in contact with the sensing surface 170 forms a top gate of the sensor 100.

The buried oxide layer 110 may comprise silicon dioxide ($SiO_2$) or the like. Materials from which the substrate 120 may be formed include, but are not limited to, silicon-on-insulator (SOI), bulk substrate, silicon carbide, silicon alloys, germanium, germanium alloys, gallium arsenide, and the like. When the substrate 120 comprises SOI, the substrate 120 forms a back gate on the sensor 100. When the substrate 120 comprises bulk substrate, however, the sensor 100 will only have the top gate comprising the solution.

The sensing element 150 may be a fin or other structure comprising a channel of undoped silicon (e.g., a silicon nanowire). The dielectric layer 162 of the gate dielectric layer 160 may comprise $SiO_2$ or the like. The metal oxide 165 of the gate dielectric layer 160 may comprise any suitable metal oxide such as hafnium dioxide ($HfO_2$) or the like.

Figure 2:
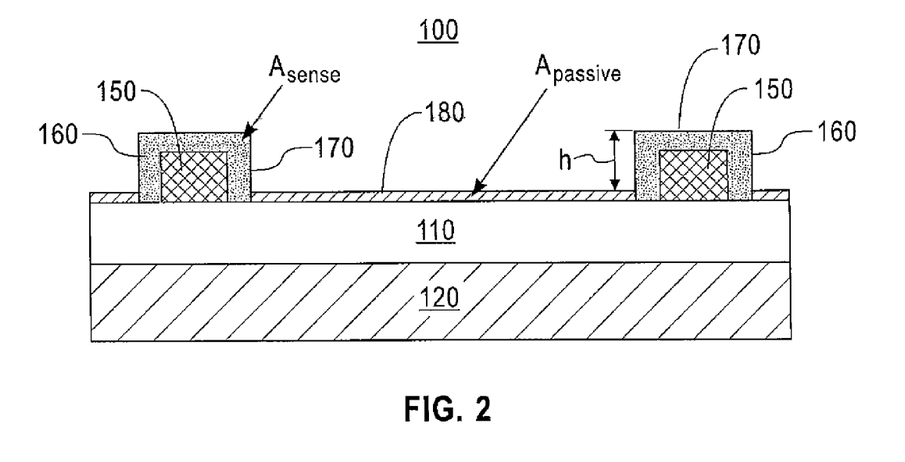
FIG. 2 is a side view of a FET-based sensor having sensing surface areas and passive surface areas comprising different materials.

As shown in FIG. 2, sensors 100 are arranged such that sensing elements 150 are positioned adjacent to (and may be surrounded by) passive surfaces 180 to define sensing areas ($A_{sense}$) and passive areas ($A_{passive}$). The passive surfaces 180 comprise $SiO_2$. As shown, the sensing element 150 with the gate dielectric layer 160 thereon may extend above the passive surface 180 by a height h to define the sensing elements 150 of the sensors 100 as fins having sidewalls and top surfaces. In other embodiments, the sensing element 150 may be planar with the passive surface 180.

Figure 3:
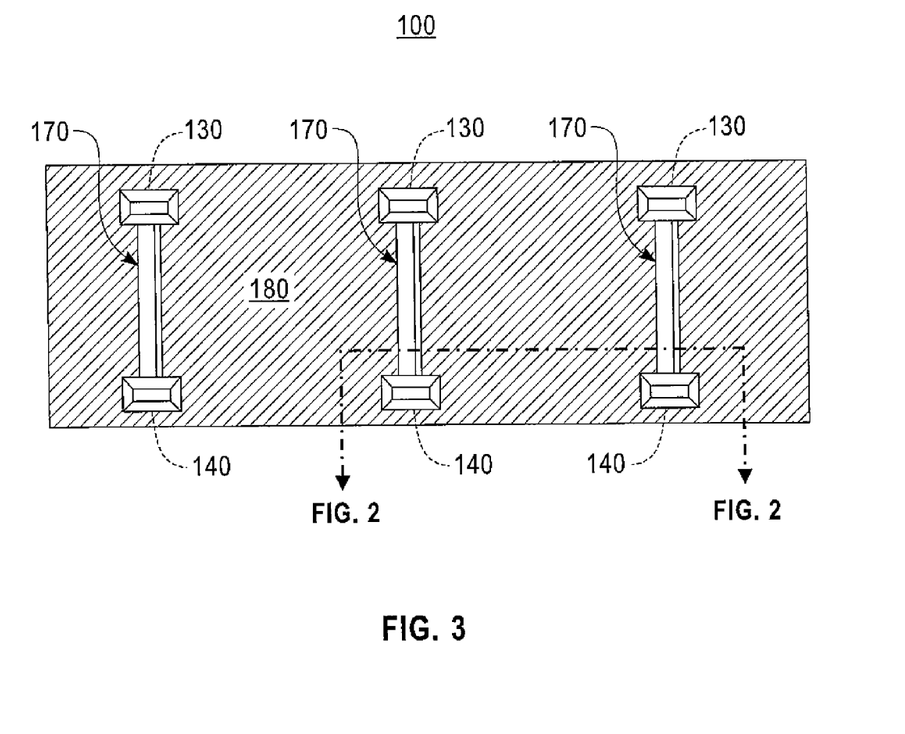
FIG. 3 is a top view of the sensor of FIG. 2.

As shown in FIG. 3, the sensing element 150 (hereinafter "fin 150") can extend between the source region 130 and the drain region 140, which are defined on the buried oxide layer 110 of the sensor 100 proximate opposing ends of the fin 150. Both the source region 130 and the drain region 140 comprise heavily doped n+ or p+ silicon. A layer of $SiO_2$ covers both the source region 130 and the drain region 140.

Referring to both FIGS. 2 and 3, the sensing surface 170 comprises antibodies self-assembled and bound to the metal oxide 165 of the gate dielectric layer 160. The antibodies are selected so as to preferentially bind to the metal oxide 165 and not to the material of the passive surface 180 (e.g., $SiO_2$). The antibodies self-assembled on and bound to the metal oxide are also selected so as to bind with specific biomolecules to be detected.

To detect the biomolecules, a drain current having exponential dependence on an applied gate voltage is measured. The majority of biomolecules are charged. Therefore, when a charged biomolecule is in the vicinity of a fin 150, the biomolecule causes the drain current to change. The change in drain current is a measure of the sensitivity of the sensor 100.

When the sensor 100 is immersed in the solution 175 (e.g., an electrolyte solution as shown in FIG. 1) that includes the biomolecules to be detected, the solution 175 in contact with the fin(s) 150 forms the top gate. The gate voltage is applied to the solution using a metal electrode (e.g., AgCl/Ag) immersed in the solution 175. In some embodiments, a positive polarity voltage is applied at the drain region 140, source voltage is held at zero, and a voltage is applied at the metal electrode, thereby causing the drain current to flow between the source region 130 and the drain region 140. When biomolecules attach to the sensing surface 170, the drain current changes, thereby allowing for the detection of the biomolecules.

In the exemplary embodiment of the present invention as shown in FIGS. 2 and 3, the likelihood of molecules of a target species in a dilute concentration not being detected due to the low probability of such a molecule binding to a surface area in a sensor is overcome or at least mitigated by providing the sensing surfaces 170 and passive surfaces 180 of the sensor 100 as dissimilar materials.

To illustrate the enhanced sensitivity of the sensor 100 (as compared to sensors in which the sensing surfaces and passive surfaces are the same material), the material of the sensing surface 170 hereinafter comprises the $HfO_2$, and the material of the passive surface 180 hereinafter comprises the $SiO_2$. Since the sensing surface 170 and the passive surface 180 comprise dissimilar materials, the chemistry of the sensing surface 170 can be selectively modified so that specific molecules or species can be targeted for binding to the sensing surface 170 without binding to the passive surface 180. With $HfO_2$ as the material of the metal oxide layer 165, the sensing surface 170 is compatible with gate dielectric layers in recent generation CMOS (complementary metal oxide semiconductor) devices. Furthermore, $HfO_2$ is compatible with current silicon technology in general.

In embodiments in which the metal oxide layer 165 is $HfO_2$ and the passive surface 180 is $SiO_2$, the sensing surface 170 can be modified such that a biomolecule of a target species is a particular protein that binds to the HfO$_2$ and not to the surrounding SiO$_2$ of the passive surface 180. After assembling the structure of the FET for the sensor 100, this modification of the sensing surface 170 comprises (i) the synthesis of a molecule that would attach to HfO$_2$ on one end and to the desired protein at the other end and (ii) self-assembly of the synthesized molecule on the metal oxide layer 165. As used herein, the term "self-assembly" refers to the ability of a molecule to autonomously attach to a surface.

One example of the modification of the sensing surface 170 employs attaching a hydroxamic acid on the HfO$_2$ of the metal oxide layer 165 to effect the synthesis and self-assembly process. A suitable hydroxamic acid can be formed by any suitable reaction mechanism (e.g., from an aldehyde in basic solution containing a sulfonamide, or by any method of coupling a hydroxylamine to a carboxylic acid). One exemplary hydroxamic acid is shown below:

The attachment of the hydroxamic acid to the HfO$_2$ of the sensing surface 170 (and not to the surrounding SiO$_2$ surface) on one end is effected by releasing the hydrogen atom from the —OH group and allowing the resulting negatively charged oxygen atom to bond to the hafnium, thereby causing the hydroxamic acid to form a film on the hafnium oxide layer in a self-assembling process. The described embodiments are not limited to the use of hydroxamic acids, however, as other acids (e.g., phosphonic acids) may be employed depending on the particular metal oxide of the metal oxide layer 165 and the desired biomolecule to be detected.

In the hydroxamic acid as shown above, R can be any hydrocarbon chain, ring, or similar ligand usable as a building block capable of giving specificity to a target molecule (e.g., a protein). In particular, R could be any antibody having an attribute suitable for binding a specific target protein. For example, the antibody could be selected so as to preferentially bind prostate specific antigen (PSA).

Figure 4:
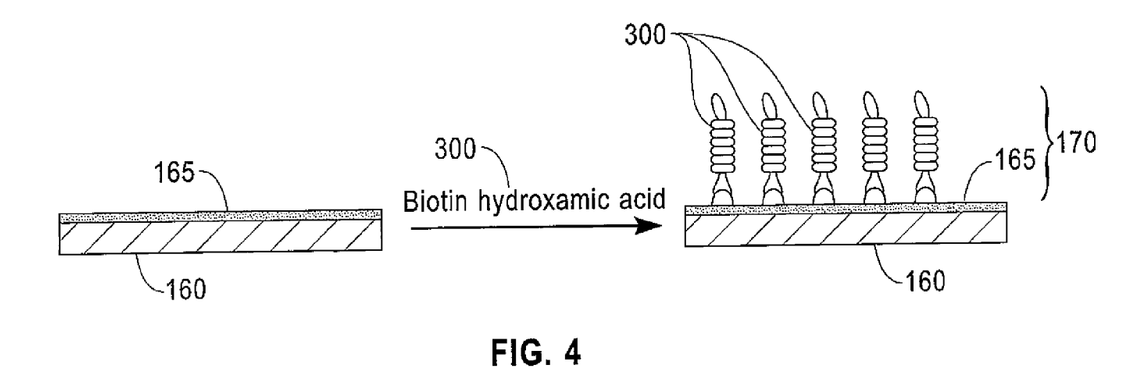
FIG. 4 is a schematic representation of an exemplary process of assembling biotin hydroxamic acid over a sensing surface area of the FET-based sensor of FIG. 2.

As shown in FIG. 4, one example of a system in which the R in the hydroxamic acid is biotin is described. Biotin is a crystalline, water-soluble vitamin (also known as Vitamin H, Vitamin B7, and Coenzyme R) having the formula $C_{10}H_{16}O_3N_2S$ that is present in small amounts in all living cells.

To build the biotin system as an example for use in the sensor 100, biotin hydroxamic acid 300 is synthesized and subsequently self-assembled as a film on the HfO$_2$ of the metal oxide layer 165 to form the sensing surface 170. The structure of the biotin hydroxamic acid 300 is shown below:

The biotin hydroxamic acid 300 is self-assembled over the HfO$_2$ of the metal oxide layer 165 to form the sensing surface 170 by removing the hydrogen atom from the —OH group and allowing the negatively charged oxygen atom to bond to the HfO$_2$, thereby forming a film of the biotin hydroxamic acid on the HfO$_2$.

Figure 5:
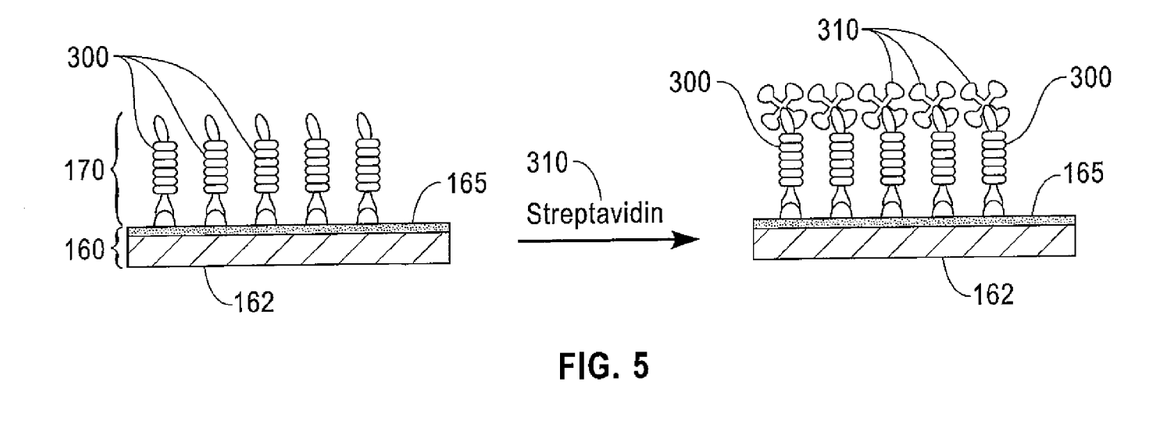
FIG. 5 is a schematic representation of an exemplary process of using the assembled biotin hydroxamic acid of FIG. 4 to detect streptavidin as the target protein.

As shown in FIG. 5, the exposure of the sensing surface 170 comprising the biotin hydroxamic acid 300 synthesized and self-assembled as the film on the HfO$_2$ allows for the detection of streptavidin 310 (as the target protein) in an aqueous solution. Streptavidin is a tetrameric protein that is isolated from the bacterium *Streptomyces avidinii* and has a high affinity for biotin. In such a system, the streptavidin 310 bonds to the biotin hydroxamic acid 300 to form a strong noncovalent biological bond.

Figure 6A:
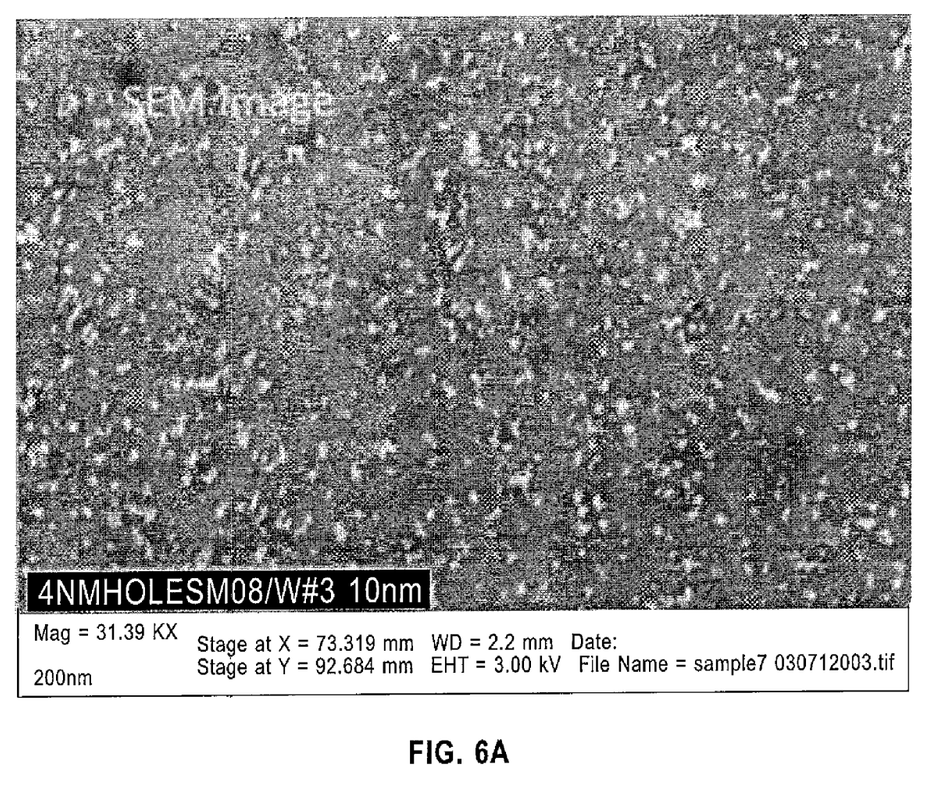
FIG. 6A is a scanning electron microscopic image of a target protein on a sensing surface area on the FET-based sensor of FIG. 2.
Figure 6B:
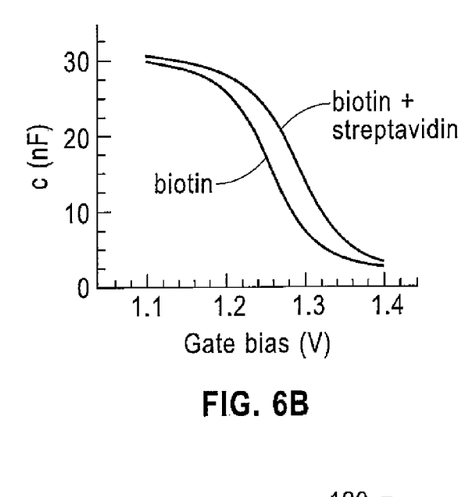
FIG. 6B is a graphical representation showing a relationship between capacitance and gate bias voltage for systems on FET-based biosensors.

As shown in FIGS. 6A and 6B, the streptavidin 310 is bound to the biotin portion of the biotin hydroxamic acid 300 coupled to the HfO$_2$. In FIG. 6A, gold nanoparticles coated with streptavidin are exposed to the HfO$_2$ surface, which has undergone the self-assembly step for biotin hydroxamic acid. Streptavidin binds to the HfO$_2$ surface, thereby indicating that the HfO$_2$ surface is coated with biotin. As a result, the scanning electron micrograph (SEM) image shows that streptavidin-coated nanoparticles bound to the HfO$_2$ surface, and that self-assembly of the biotin hydroxamic acid 300 occurs as a monolayer on the HfO$_2$ of the sensing surface 170. A similar experiment was carried out with regard to the SiO$_2$ of the passive surface 180. However, an analogous self-assembly of the biotin hydroxamic acid 300 is not observed for the SiO$_2$ of the passive surface 180.

In FIG. 6B, capacitance-voltage (C-V) is measured for the HfO$_2$ covered with the biotin hydroxamic acid 300 before and after exposure of the sensing surface 170 to the streptavidin 310. A flatband voltage for the C-V curve shifts when the biotin-coated HfO$_2$ surface is exposed to streptavidin protein in solution. The change in the flatband voltage implies that the streptavidin is binding to the biotin-coated HfO$_2$ surface. Such a change in flatband voltage causes the drain current (the sensing current) in the sensor 100 to vary. Analogous shifting on the SiO$_2$ of the passive surface 180 does not occur.

Similar schemes using other hydroxamic acids in which R is a different ligand can be carried out for other target species. For example, metal oxides other than the HfO$_2$ can be disposed on the sensing surface 170, and such metal oxides may be coated with hydroxamic acids in which the R is an antibody that would bind a targeted protein such as PSA. The R may be any other ligand capable of binding other target species including, but are not limited to, DNA, RNA, and the like.

By way of an additional example of the modification of the sensing surface 170, a self-assembly process can utilize octadecane hydroxamic acid (ODHA) on the HfO$_2$ of the sensing surface 170. The ODHA is a hydroxamic acid (as shown above) in which R is $CH_3(CH_2)_{16}$.

Figure 7A:
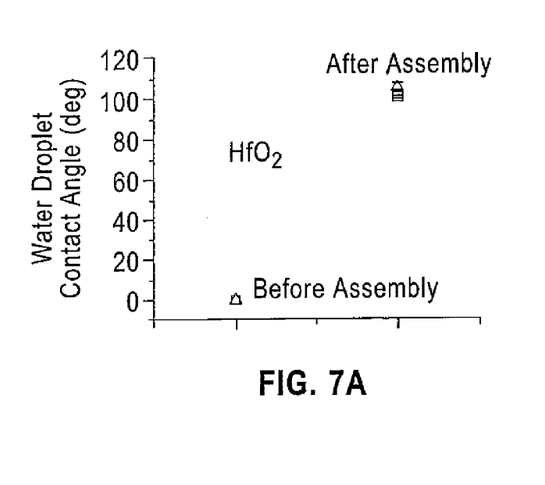
FIG. 7A is a graphical representation indicating the self-assembly of octadecane hydroxamic acid on hafnium dioxide.
Figure 7B:
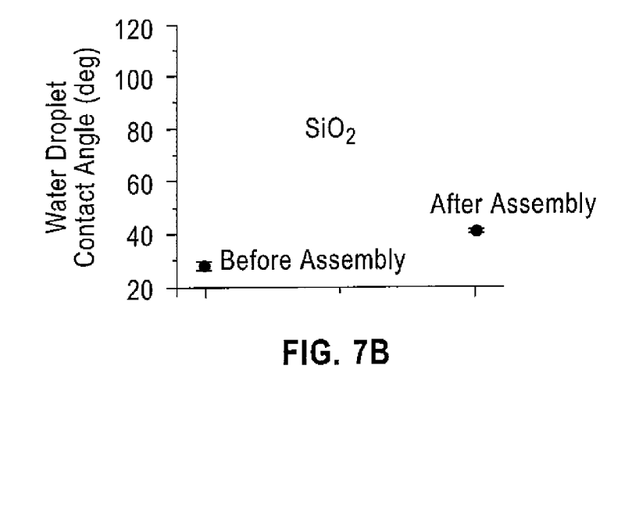
FIG. 7B is a graphical representation illustrating a lack of self-assembly of octadecane hydroxamic acid on silicon dioxide.

The assembly of the ODHA on the HfO$_2$ can be studied using, for example, a water droplet contact angle measurement technique. In such a technique, because the ODHA is hydrophobic, the expected contact angle for self-assembly of ODHA on the HfO$_2$ is greater than 90 degrees. As shown in FIG. 7A, the contact angle of the ODHA on the HfO$_2$ is determined to be about 110 degrees, accordingly indicating the self-assembly of ODHA on the HfO$_2$. In contrast, as shown in FIG. 7B, the contact angle of the ODHA on the SiO$_2$ is determined to be about 40 degrees, which indicates the lack of self-assembly of ODHA on the SiO$_2$. Although the self-assembly of the ODHA on HfO$_2$ is described to illustrate the synthesis of the ODHA on the HfO$_2$ and not on the SiO$_2$, the ODHA assembled on the HfO$_2$ may function as a receptor for a suitable target species.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical applications, and to enable others of ordinary skill in the art to understand the invention for various embodiments with various modifications as are suited to the particular uses contemplated.

The invention claimed is:

1. A method of forming a sensor, comprising:
    disposing a silicon sensing fin on a buried oxide layer of a substrate to form a channel of undoped silicon for providing a current flow between a source region and a drain region, each of the source region and the drain region comprising heavily doped silicon;
    depositing a dielectric layer and a metal oxide on one or more sides and a top of the sensing fin, the dielectric layer and the metal oxide forming a sensing surface on the silicon sensing fin;
    depositing a passive surface over the buried oxide layer and surrounding, adjacent to, or around the sensing fin, a material of the passive surface being different from a material of the sensing surface;
    modifying the sensing surface opposite the substrate with a compound bound to the sensing surface on the sensing fin and not bound to the passive surface, the compound having a ligand specifically configured to preferentially bind a target biomolecule; and
    causing a change in current flow between the source region and the drain region to sense the target biomolecule on the sensing surface.

2. The method of claim 1, wherein depositing a dielectric layer on the silicon sensing fin to form the sensing surface comprises depositing a layer of $HfO_2$.

3. The method of claim 2, wherein depositing a passive surface over the buried oxide layer surrounding, adjacent to, or around the sensing fin comprises depositing a layer of $SiO_2$ on the substrate.

4. The method of claim 2, wherein modifying the sensing surface to preferentially bind the target biomolecule comprises causing a molecule to self-assemble on the sensing surface.

5. The method of claim 4, wherein causing the molecule to self-assemble on the sensing surface comprises binding a hydroxamic acid to the sensing surface.

6. The method of claim 5, wherein the hydroxamic acid bound to the sensing surface comprises an antibody having an attribute suitable for preferentially binding a specific target protein as the target biomolecule.

* * * * *